(12) United States Patent
Brewer et al.

(10) Patent No.: US 9,078,987 B2
(45) Date of Patent: Jul. 14, 2015

(54) CLUTCH BRAKE ASSEMBLY FOR A RESPIRATORY ACCESS PORT

(75) Inventors: John Brewer, Marietta, GA (US);
Cassandra E. Morris, Roswell, GA (US); Joe Gordon, Mansfield, MA (US);
David Zitnick, Providence, RI (US)

(73) Assignee: Avent, Inc., Alpharetta, GA (US)

( * ) Notice: Subject to any disclaimer, the term of this patent is extended or adjusted under 35 U.S.C. 154(b) by 832 days.

(21) Appl. No.: 13/336,126

(22) Filed: Dec. 23, 2011

(65) Prior Publication Data

US 2013/0160770 A1    Jun. 27, 2013

(51) Int. Cl.
*A61M 16/00*    (2006.01)
*A61M 16/04*    (2006.01)
*A61M 16/08*    (2006.01)

(52) U.S. Cl.
CPC ....... *A61M 16/0463* (2013.01); *A61M 16/0816* (2013.01); *A61M 16/0833* (2014.02)

(58) Field of Classification Search
CPC ..................... A61M 16/0463; A61M 16/0816; A61M 16/0833; A61M 16/0841; A61M 16/085; A61M 16/0858; A61M 25/0111; A61M 25/0014; A61M 2025/0026; A61M 39/223; A61M 39/1011
USPC ............. 604/200.26, 207.14–207.17, 200.24, 604/205.24
See application file for complete search history.

(56) References Cited

U.S. PATENT DOCUMENTS

| | | |
|---|---|---|
| 4,270,778 A | 6/1981 | Brownell |
| 4,326,520 A | 4/1982 | Alley |
| 4,569,344 A | 2/1986 | Palmer |
| 4,641,646 A | 2/1987 | Schultz et al. |
| 4,836,199 A | 6/1989 | Palmer |
| 5,158,569 A | 10/1992 | Strickland et al. |
| 5,207,641 A | 5/1993 | Allton |
| 5,255,672 A | 10/1993 | Jinotti |
| 5,309,902 A | 5/1994 | Kee et al. |
| 5,333,606 A | 8/1994 | Schneider et al. |
| 5,333,607 A | 8/1994 | Kee et al. |
| 5,335,655 A | 8/1994 | Kee |
| 5,337,780 A | 8/1994 | Kee |
| 5,343,857 A | 9/1994 | Schneider et al. |
| 5,354,267 A | 10/1994 | Niermann et al. |
| 5,357,946 A | 10/1994 | Kee et al. |
| 5,377,672 A | 1/1995 | Kee |
| 5,445,141 A | 8/1995 | Kee et al. |
| 5,540,668 A | 7/1996 | Wilson, Jr. et al. |

(Continued)

FOREIGN PATENT DOCUMENTS

| | | |
|---|---|---|
| DE | 29 39 794 A1 | 4/1981 |
| DE | 40103300.0001 D | 8/2001 |

(Continued)

*Primary Examiner* — Lynne Anderson
*Assistant Examiner* — Bradley Philips
(74) *Attorney, Agent, or Firm* — Dority & Manning, P.A.

(57) ABSTRACT

A respiratory access assembly includes a distal plate having a port, the port adapted to be positioned in operable communication with an artificial airway of a patient. The assembly also includes a proximal plate including a first port and a second port and, when the distal plate is positioned against the proximal plate in a stacked configuration, each plate is configured to move relative to the other. There is a clutch positioned between the plates, the clutch cooperating with both plates to substantially prevent movement of the plates when the port of the distal plate is positioned in an alignment with at least one port of the proximal plate and an object is positioned through the aligned ports of the plates.

8 Claims, 7 Drawing Sheets

(56) References Cited

U.S. PATENT DOCUMENTS

| | | |
|---|---|---|
| 5,628,306 A | 5/1997 | Kee |
| 5,643,294 A | 7/1997 | Tovey et al. |
| 5,694,922 A | 12/1997 | Palmer |
| 5,730,123 A | 3/1998 | Lorenzen et al. |
| 5,735,271 A | 4/1998 | Lorenzen et al. |
| 5,738,091 A | 4/1998 | Kee et al. |
| 5,746,199 A | 5/1998 | Bayron et al. |
| 5,882,348 A | 3/1999 | Winterton et al. |
| 5,916,201 A | 6/1999 | Wilson, Jr. et al. |
| 6,012,451 A | 1/2000 | Palmer |
| 6,070,582 A | 6/2000 | Kee |
| D448,842 S | 10/2001 | Madsen et al. |
| D448,843 S | 10/2001 | Madsen et al. |
| D449,106 S | 10/2001 | Madsen et al. |
| D449,107 S | 10/2001 | Madsen et al. |
| 6,494,203 B1 | 12/2002 | Palmer |
| 6,543,451 B1 | 4/2003 | Crump et al. |
| 6,588,421 B1 | 7/2003 | Diehl |
| 6,609,520 B1 | 8/2003 | Carlsen et al. |
| 6,612,304 B1 * | 9/2003 | Cise et al. ............... 128/200.26 |
| 6,615,835 B1 | 9/2003 | Cise et al. |
| 6,629,530 B2 | 10/2003 | Cise |
| 6,698,424 B2 | 3/2004 | Madsen et al. |
| 6,729,326 B1 | 5/2004 | Winterton et al. |
| 6,811,142 B2 | 11/2004 | Svendsen |
| 6,923,184 B1 | 8/2005 | Russo |
| 6,978,783 B2 | 12/2005 | Svendsen |
| 7,021,313 B1 | 4/2006 | Crump et al. |
| 7,188,623 B2 | 3/2007 | Anderson et al. |
| 7,191,782 B2 | 3/2007 | Madsen |
| 7,263,997 B2 | 9/2007 | Madsen et al. |
| 7,353,822 B2 | 4/2008 | Van Hooser et al. |
| 2004/0221852 A1 | 11/2004 | Madsen |
| 2005/0199243 A1 | 9/2005 | Svendsen |
| 2009/0287151 A1 * | 11/2009 | Resca ............... 604/119 |
| 2010/0147310 A1 * | 6/2010 | Brewer et al. ............ 128/207.14 |
| 2010/0147312 A1 * | 6/2010 | Brewer et al. ............ 128/207.14 |
| 2010/0288282 A1 * | 11/2010 | Brewer et al. ............ 128/207.14 |

FOREIGN PATENT DOCUMENTS

| | | |
|---|---|---|
| DE | 40103300.0002 D | 8/2001 |
| DE | 40103300.0003 D | 8/2001 |
| DE | 40103300.0004 D | 8/2001 |
| EP | 1 208 865 A2 | 5/2002 |
| EP | 0 812 220 B1 | 5/2004 |
| EP | 0 805 694 B1 | 6/2007 |
| FR | 000012046.0001 D | 8/2001 |
| FR | 000012048.0001 D | 8/2001 |
| FR | 000012049.0001 D | 8/2001 |
| FR | 000012050.0001 D | 8/2001 |
| GB | 1 443 152 A | 7/1976 |
| GB | 2 061 465 A | 5/1981 |
| GB | 002100746 D | 8/2001 |
| GB | 002100747 D | 8/2001 |
| GB | 002100748 D | 8/2001 |
| GB | 002100749 D | 8/2001 |
| WO | WO 93/21981 A2 | 11/1993 |
| WO | WO 95/31240 A1 | 11/1995 |
| WO | WO 95/31249 A1 | 11/1995 |
| WO | WO 95/31250 A1 | 11/1995 |
| WO | WO 96/22118 A1 | 7/1996 |
| WO | WO 96/26757 A1 | 9/1996 |
| WO | WO 98/10808 A2 | 3/1998 |
| WO | WO 98/33536 A1 | 8/1998 |
| WO | WO 99/19013 A1 | 4/1999 |
| WO | WO 01/21241 A1 | 3/2001 |
| WO | WO 01/76659 A1 | 10/2001 |
| WO | WO 01/76673 A1 | 10/2001 |
| WO | WO 02/28463 A2 | 4/2002 |
| WO | WO 02/051485 A1 | 7/2002 |
| WO | WO 2004/101044 A1 | 11/2004 |
| WO | WO 2006/133882 A1 | 12/2006 |
| WO | WO 2007/141487 A1 | 12/2007 |

* cited by examiner

CLUTCH BRAKE ASSEMBLY FOR A RESPIRATORY ACCESS PORT

BACKGROUND

The disclosures herein relate generally to improved medical care for intubated patients, and more particularly to a novel multiple access respiratory port, assembly, manifold, fitting, adaptor, connector and/or access control assembly, and related methods, for ventilating, aspirating, monitoring, sampling, and providing therapeutic delivery to the respiratory tracts of intubated patients, including infants, adolescents, and adults.

Respiratory patient care is a dynamically developing field in medicine, ranging in its needs from infants to the aged. The ranges of respiratory ailments, both temporary and permanent, to which such patients are subjected, are many and varied. For example, the range of procedures for intubated patients may include the following: ventilation, aspiration, oxygenation, sampling, visual inspection, in-line sensing, pressure monitoring, flushing, medicating and/or lavage. Most problems now center or focus on multiple needs of the patient and the accommodation of multiple treatments, some to be performed at the same time. The lack of equipment to easily, efficiently, and safely accomplish the multiple therapies in the best interest of the patient has been and continues to be a concern. It is strongly preferred that these procedures be carried out while the patient continues to be ventilated mechanically. Removal of ventilator assistance could result in a drop in blood oxygen levels with resulting danger to the patient.

In low lung capacity patients, such as premature babies and adults suffering from emphysema, one problem is the removal of accumulated lung secretions. It is undesirable to starve such patients of oxygen during the secretion removal process. Secretion removal is accomplished via a suction catheter which is temporarily positioned via a respiratory access assembly in an artificial airway, i.e., an endotracheal tube placed in a portion of the patient's respiratory tract to provide air (oxygen and other gases) to the lungs of such patients. While this procedure sounds simple, it is fraught with difficulties, particularly when a caregiver must change devices or perform other therapeutic treatments sequentially or simultaneously. In fact, these difficulties may result in the patient contracting ventilator acquired pneumonia (VAP). In addition, failure to adequately seal a respiratory access assembly may cause a compromise of positive end-expiration pressure (PEEP), which in turn may cause sub-optimal ventilation.

One way of addressing these problems is with the use of a rotatable multiple access manifold or "assembly" as the respiratory access assembly. The assembly is adapted to be positioned in operable communication with an artificial airway of a patient and to allow for the connection of multiple devices that may be passed into the respiratory tract of a patient while the patient remains connected to the ventilator. The assembly comprises a distal plate having a port. The assembly includes a proximal plate, which has a first port and a second port. The distal plate is positioned against the proximal plate in a stacked configuration, and each plate is configured to move with respect to the other plate. The assembly may rotate to allow access to the endotracheal tube for multiple devices that may be attached to the proximal plate.

An issue that has arisen in the use of such assemblies is that it is possible, using excessive force, to rotate the assembly before an inserted device has been completely withdrawn. In this case it is possible to sever or slice off a piece of the device, such as a catheter. If this occurs the piece can disrupt the flow of air to the patient or, in extreme cases, travel into the respiratory tract of the patient. It is important in the use of the multiple access assembly that the device be fully withdrawn prior to allowing rotation of the assembly. There is a need to address and overcome these difficulties, preferably with a passive design that functions without the need for operator intervention.

SUMMARY

In response to the difficulties and problems discussed herein, a respiratory access assembly is provided, wherein the assembly has two plates with respective ports and a clutch that is positioned adjacent to at least one plate. The clutch cooperates with both plates to substantially prevent movement of the plates when the port of the distal plate is aligned with at least one port of the proximal plate and an object is positioned through the aligned ports of the plates.

The clutch is activated only when an object is positioned through the aligned ports to substantially prevent movement of the plates, thereby providing a passive lock. When the object is positioned through the aligned ports, the clutch pivots about a point on one of the plates, for example the distal plate, and a region on the clutch, a tooth surface, contacts a tooth on that plate while simultaneously moving on a ramp on that plate toward the other plate. The clutch includes a pin that can contact a stop provided on the plate without the tooth and ramp. The stop is configured to prohibit movement of the clutch by acting on the pin when an object is positioned through the aligned ports.

The clutch acts to stop the movement of the two plates relative to each other when an object such as a catheter is inserted because the catheter contacts the clutch and moves it in a direction that causes a tooth surface on the clutch to contact a tooth on the distal plate when the plates are turned. The clutch and the distal plate are thus unable to move relative to each other. Simultaneously with this movement, as the clutch is moved by the catheter, the clutch also contacts a ramp on the distal plate and this causes the clutch to move up the ramp toward the proximal plate. As the clutch moves toward the proximal plate, a pin on the clutch moves upwardly until it is high enough to interfere with, i.e. touch, one of the stops on the distal surface of the proximal plate. When the pin contacts a stop, the movement of the plates relative to each other ceases.

3C is a view of the proximal side of the distal plate showing the port, central alignment point, ramp, tooth and rim.

Figure 4:
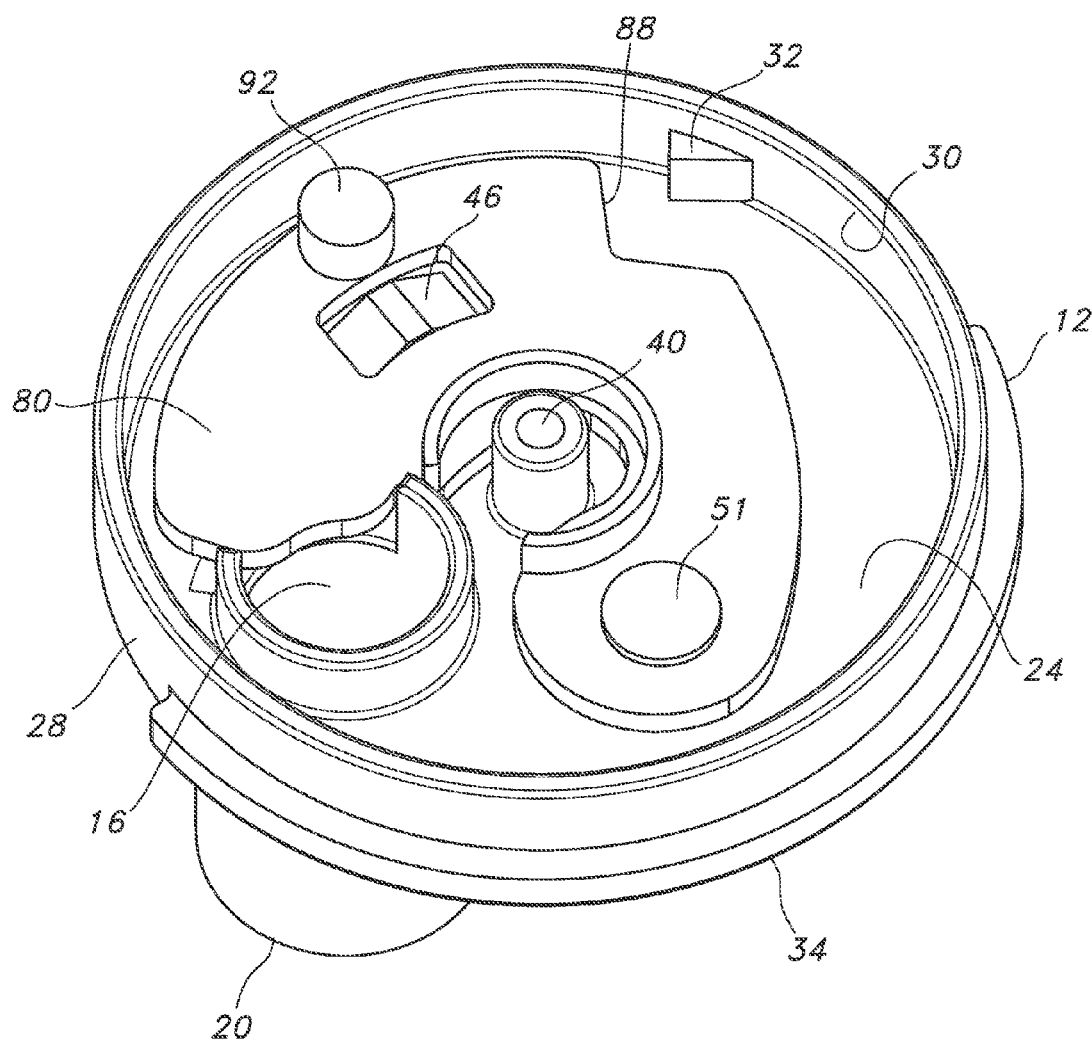

FIG. 4 is a proximal view of the distal plate showing the cooperation of the distal plate and the clutch. The position of the tooth and ramp of the distal plate relative to the clutch are clearly visible. The central alignment point of the plate is visible as well and it is clear that the clutch does not contact or interfere with central alignment point.

Figure 5A:
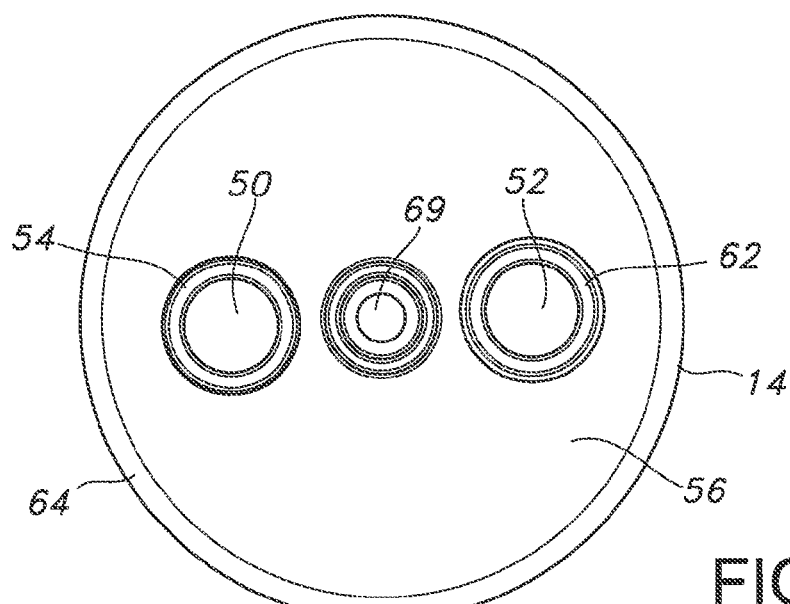
Figure 5B:
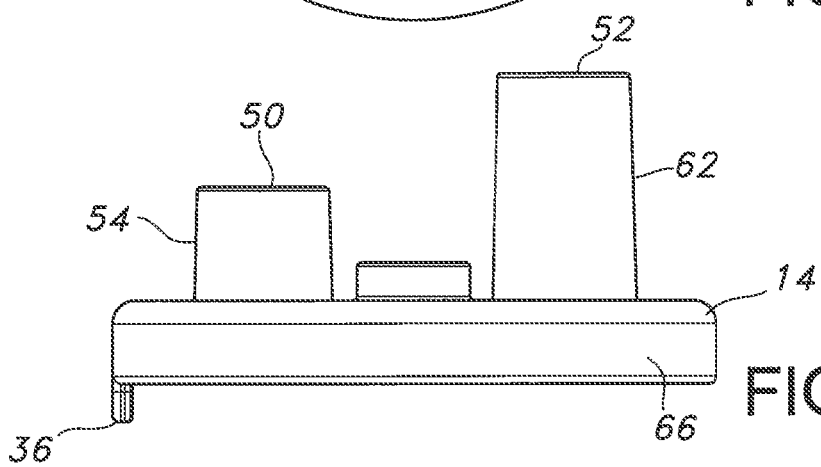
Figure 5C:
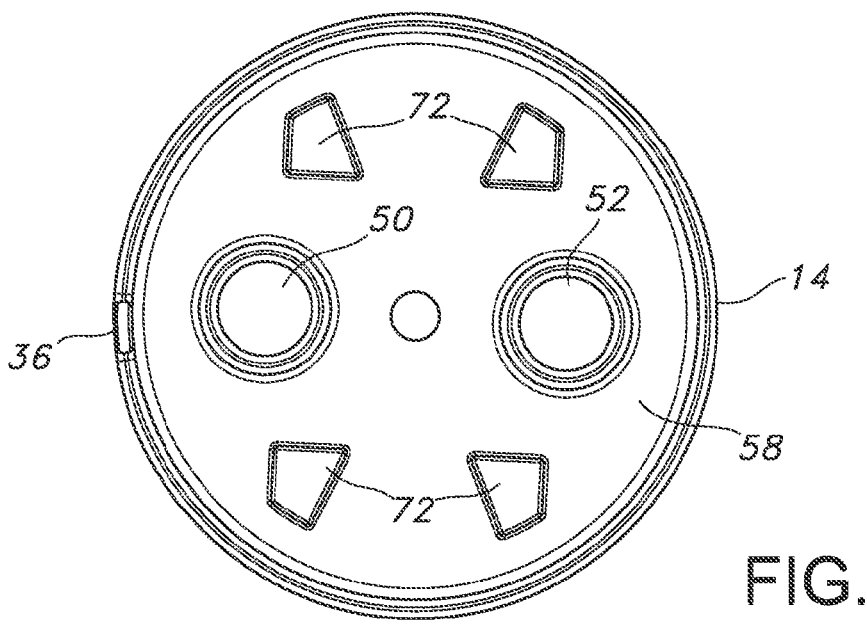

FIG. 5 includes three views of the proximal plate. FIG. 5A is a view of the proximal side of the proximal plate showing two ports and a central alignment point. FIG. 5B is a side view of the proximal plate, again showing the ports as well as a tab on the perimeter wall of the proximal plate extending in a distal direction. The tab on the proximal plate contacts the most distant ends of the rim on the distal plate to limit movement of the two plates relative to each other. FIG. 5C is a view of the distal side of the proximal plate showing the stops that cooperate with the pin on the clutch to prohibit movement of the clutch relative to the plate.

Figure 6:
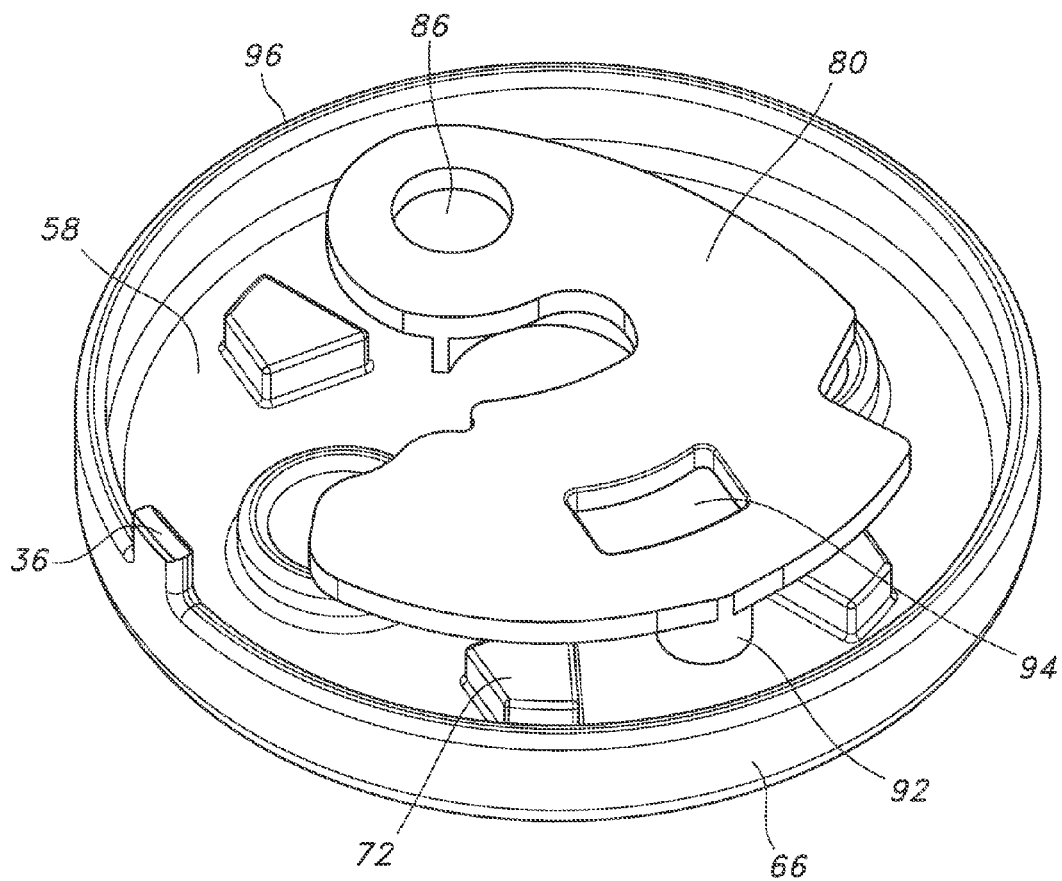

FIG. 6 is a distal view of the proximal plate showing the cooperation of the proximal plate and the clutch. The pin on the clutch is shown between two stops on the proximal plate. The pin can move freely past the stops unless an object is inserted into a port on the plate and rotation of the plates relative to each other is attempted, in which case the pin is forced upwardly and contacts a stop to prohibit movement of the clutch relative to the plate.

Figure 7A:
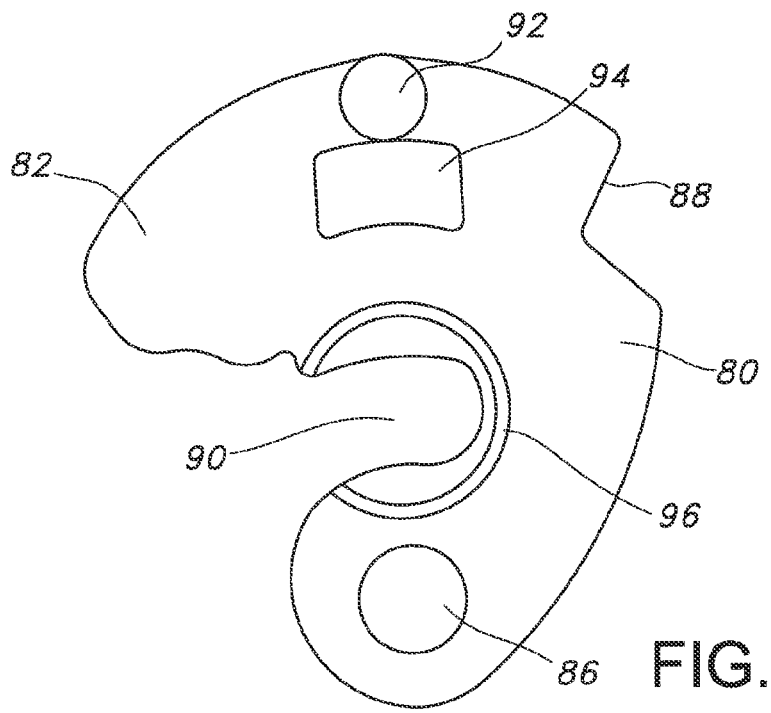
Figure 7B:
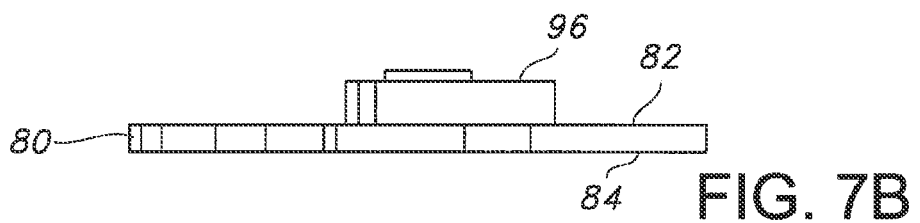
Figure 7C:
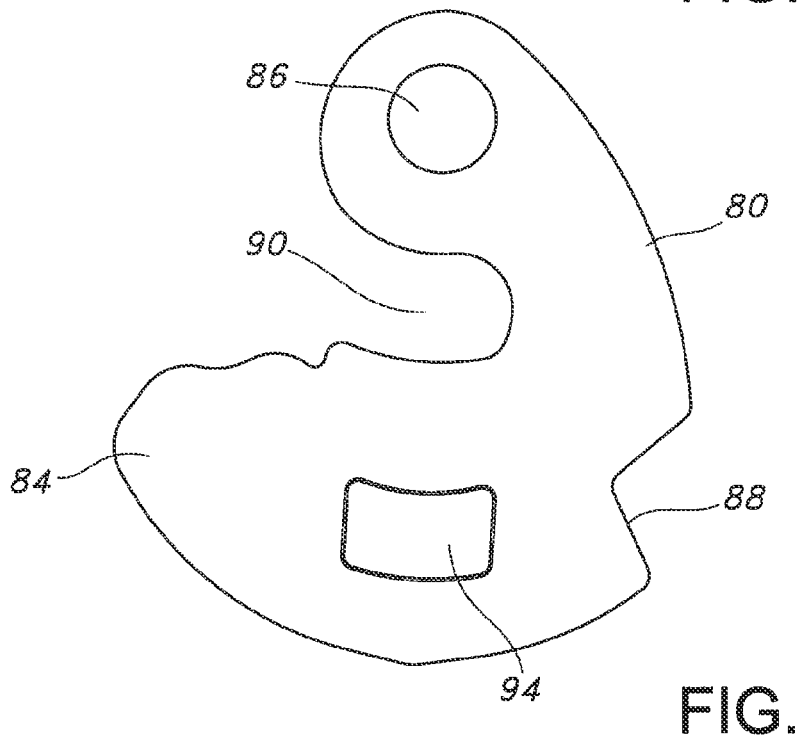

FIG. 7 includes three views of the clutch. FIG. 7A is a view of the proximal surface of the clutch showing the pin which will contact the proximal plate when the clutch moves up the ramp on the distal plate when an object is inserted into a port on the plate and rotation is attempted. FIG. 7B is a side view of the clutch. FIG. 7C is a view of the distal side of the clutch showing the opening for the ramp of the distal plate and the pivot point about which the clutch moves.

DETAILED DESCRIPTION

Reference will now be made in detail to one or more embodiments, examples of which are illustrated in the drawings. Each example and embodiment is provided by way of explanation and is not meant as a limitation. For example, features illustrated or described as part of one embodiment may be used with another embodiment to yield still a further embodiment.

The present respiratory access port assembly operates in a closed ventilating system and is designed to accommodate multiple points of access to the respiratory system of an intubated patient without compromising the closed circuit character of the closed system and without interruption of the flow of ventilating gases to the patient.

Access to the closed respiratory system through one or more access sites is provided, for example, to ventilate the lungs of the patient with gas or gases, to aspirate secretions from the lungs using a suction catheter, to oxygenate the lungs to eliminate or reduce residual carbon dioxide therefrom, to visually inspect selected parts of the patient's respiratory system, to sample sputum and gases, to sense parameters such as flow rates, pressure, and/or temperature, to flush with solution(s), and to administer medication, gases, and/or lavage.

As used herein the term "suction catheter" means long, flexible tubes used to remove secretions from the airway and are available in many sizes, typically from 10 to 25 inches (25 to 64 cm) in length. Suction catheters are flexible and may be made from latex and other soft polymers. The inner and outer diameters will vary according to the catheter size chosen by a user as appropriate for his particular application, e.g. pediatric or adult. Catheter sizes are usually expressed as "French" and common catheter sizes range from a 5 French to an 18 French. (Note that French is a measure of circumference based on the theory that non-round tubes of the same circumference will fit into the same incision. One French is approximately 0.33 mm or 0.013 inch). The catheter may generally have an outer diameter of about 0.165 to about 0.205 inch (4.19 to about 5.21 mm).

Suction catheters are well known and widely commercially available for many medical uses. Suctioning may be performed using an "open" or "closed" system. In the open system, the suction catheter is merely a flexible plastic tube that is inserted into a tracheal tube like an endotracheal tube or tracheostomy tube, with a source of suction connected to the proximal end of the suction catheter. Anything that the suction catheter touches before entering the lumen must be maintained in a sterile condition so a "sterile field" must be created on or next to the patient. The suction catheter must be carefully handled after it is used since it will be coated with the patient's secretions.

In contrast, in the "closed" system, for example that disclosed in commonly owned U.S. Pat. No. 4,569,344, a device which may be used to suction secretions is enclosed within a generally cylindrical plastic bag to eliminate or minimize contamination of the suction catheter prior to use. This is generally referred to as a "closed suction catheter" device and is available under the trade name TRACH CARE® from BALLARD® Medical Products (Kimberly-Clark Corporation) or KIMVENT®. As the patient requires artificial removal of secretions, the suction catheter may be advanced through one end of the plastic bag, through a connecting fitting or manifold and into the tracheal tube. The other, proximal end of the suction catheter is attached to a source of suction. Suction may be applied using, for example, a finger controlled valve on the proximal end of the suction catheter, and the secretions removed.

Secretions are thus drawn into the lumen of the suction catheter tube and removed and the system remains closed. The suction catheter is subsequently withdrawn from the flexile lumen and back into the plastic bag to keep the circuit closed. Closed suction systems are generally preferred by healthcare providers since the provider is better protected from the patient's secretions. Closed suction systems are also easier and quicker to use since a sterile field need not be created each time the patient must be suctioned, as is required in open suction systems. The closed suction catheter may be permanently attached to the proximal end of the tracheal tube or may be detachably connected so that it may be replaced periodically.

Examples of other types of generally tubular objects that may be inserted into the tracheal tube and thence into the lungs include bronchoscopes and bronchoalveolar lavage (BAL) catheters. One type of bronchoalveolar lavage catheter is commercially available under the trade name BAL CATH® from Ballard Medical Products Inc., a division of Kimberly-Clark Corporation and may be used for lavage and sampling of the lungs to assist in the diagnosis of ventilator acquired pneumonia.

Many current designs for respiratory access port assemblies may have only one port. This port is generally used for suctioning secretions from the lungs as discussed above and, in these instances, the suction catheter must be removed when other tasks need to be performed, such as, for example, bronchoscopy, bronchial alveolar lavage, and so on. Opening a closed ventilating system by removing the suction catheter on such a ventilated patient can lead to infection, as noted previously.

Also, current designs of multiple access port manifolds and/or assemblies do not contain a safety lock. In certain instances, due to the lack of such a safety lock, the introduction of a suction catheter through a manifold port may result in a portion of the catheter being severed or cut off and aspirated into the patient's lungs. This can lead to significant complications, including airway blockage, infection, and even death. Further, failure to adequately seal a respiratory access assembly may cause a compromise of positive end-expiration pressure (PEEP), which in turn may cause suboptimal ventilation which can result in collapsing alveoli in the patient's lungs. The present respiratory access assembly includes features which permit multiple points of access without opening the closed ventilation system, and it contains a passive safety lock feature which prevents severing or loss of any portion of the suction catheter and/or other object while it is positioned within the assembly.

Figure 1:
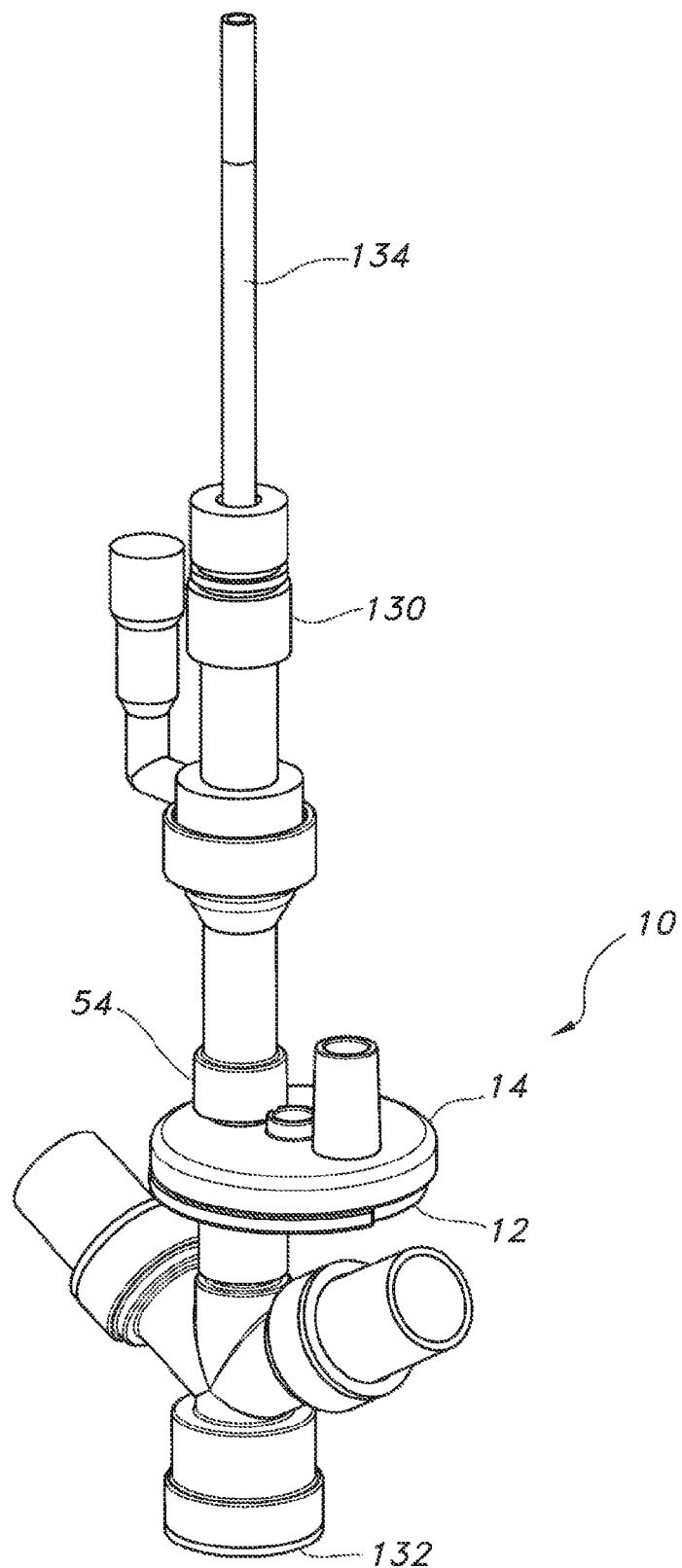
FIG. 1 is a perspective view of a respiratory access assembly of the present disclosure, illustrating the assembly coupled to a respiratory manifold which is connected to an artificial airway at a distal end of the assembly, and showing a portion of a suction catheter assemblage coupled to a proximal end of the respiratory access assembly. The suction catheter may be advanced through the assembly into the respiratory tract of a patient when the assembly is in the proper alignment.
Figure 2:
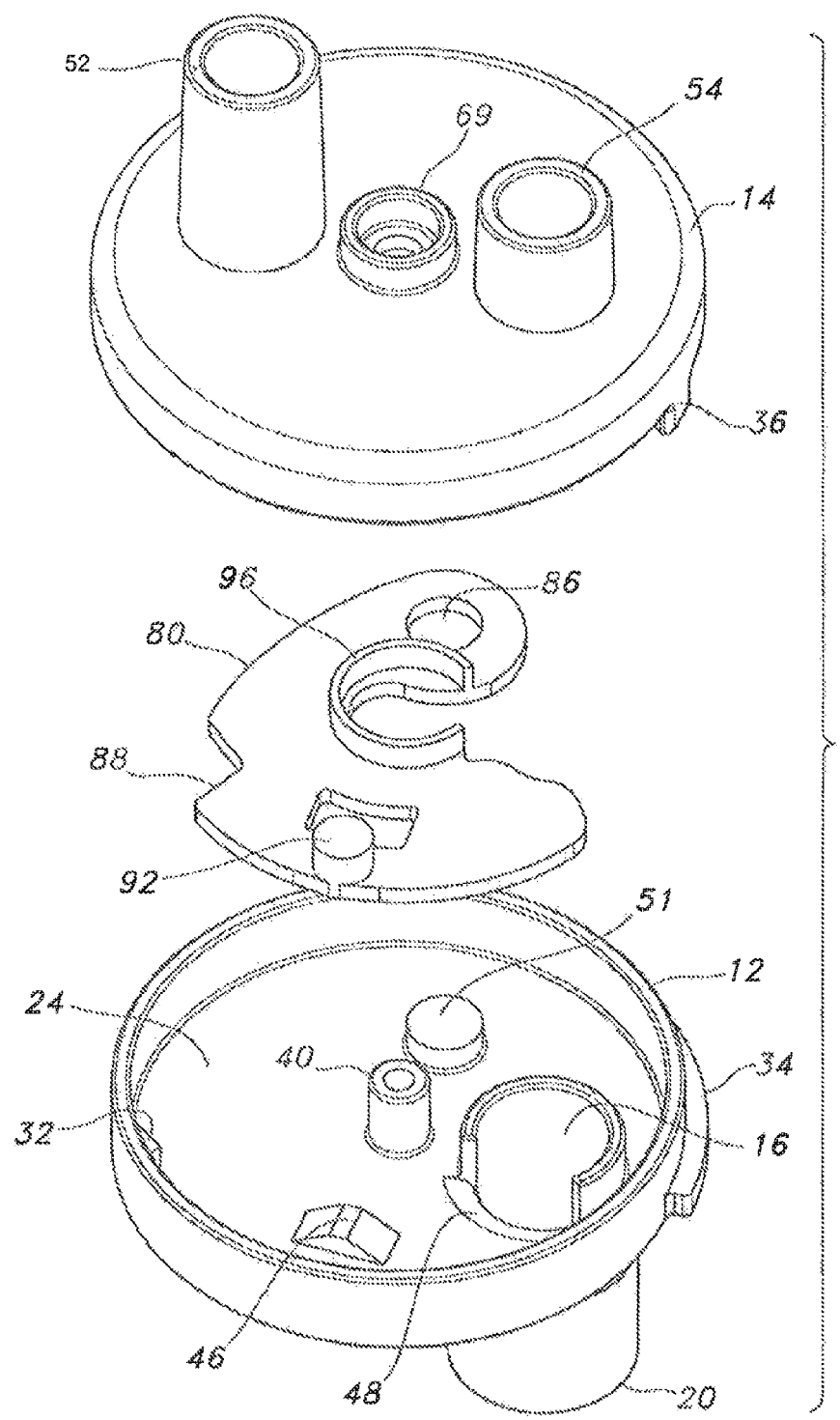
FIG. 2 is an exploded perspective view of the respiratory assembly of FIG. 1 showing the proximal and distal plates and the clutch between them.

Turning now to the drawings, as illustrated in FIG. 1, a respiratory access assembly 10 is provided. The assembly 10, as shown in FIGS. 1 and 2, includes a distal disk or plate 12 and a proximal disk or plate 14 which are positioned next to each other in a stacked and axially aligned configuration, as well as a clutch 80 between them. The terms "align," "alignment," and variations thereof desirably refer to the spatial property possessed by an arrangement or position of things in a straight line. The terms "configure" or "configuration" and derivatives thereof desirably refer to the design, arrangement, set up, or shape with a view to specific applications or uses.

Figure 3A:
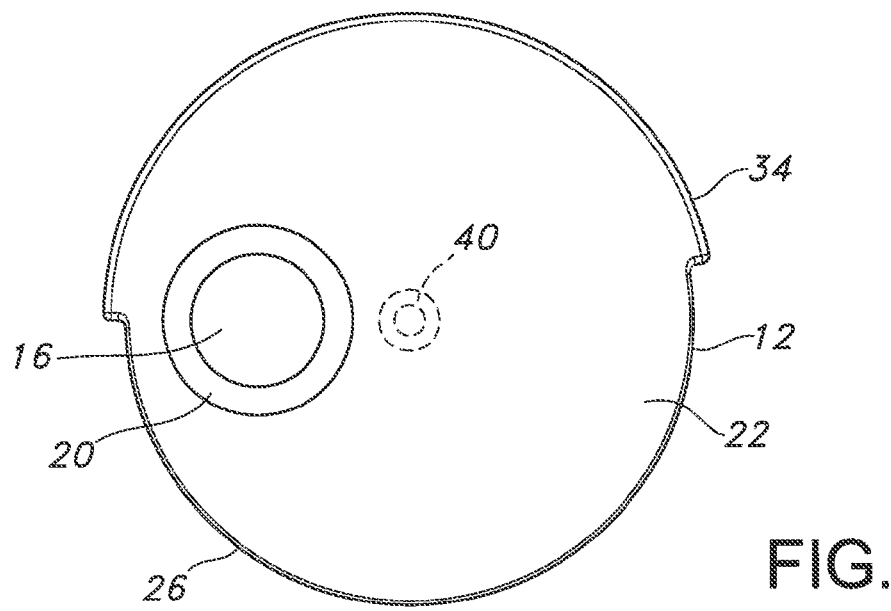
FIG. 3A is a view of the distal side of the distal plate showing a port, a central alignment point and a rim that extends partially around the perimeter of the plate.

The distal disk or plate 12 includes at least one port 16 having an opening formed through the disk or plate 12, as illustrated in FIGS. 3 and 4. A cuff, such as cuff 20, may, for example, be provided on an outer distal surface 22 of the disk or plate 12. Such a cuff 20 generally encircles the port 16 and the opening extends through it (the cuff 20) such that the cuff 20 provides a portion of the port 16 (FIG. 3A). The cuff 20 can extend through the proximal surface 24 of the distal plate 12 in a proximal direction though it has a cut-out portion arranged 48 so that the clutch 80 can contact a catheter inserted through the port 16.

The term "port" as used herein means an opening into or through a component for the passage of an object and/or a liquid and/or a gas. The term "cuff" as used herein means a generally cylindrical component having an opening through it and which is positioned over a port and forms a portion of the port. Further, it will be understood that a port and its cuff may collectively be given the term herein of "port", and two or more ports, each with its associated cuff, may collectively be given the term herein of "ports".

The term "plate" or "disk" as used herein refers to any shape and configuration of a plate, including, but not limited to, round, square, rectangular, and so forth. It should be understood that a plate or disk may be arced, arched, planar, convex, concave, and so forth.

Figure 3B:
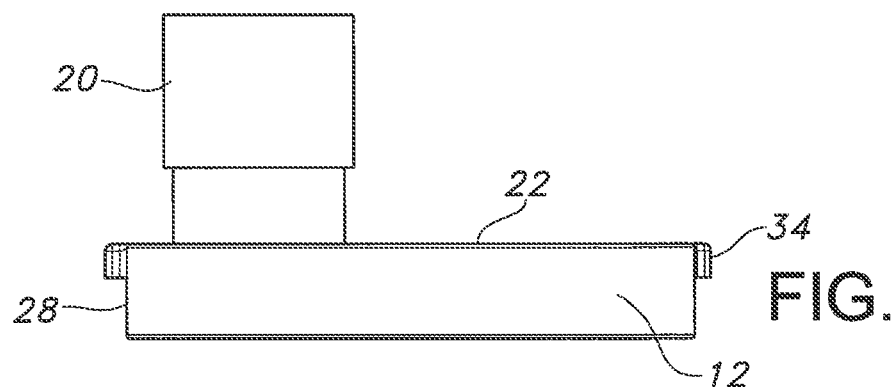
FIG. 3B is a side view of the distal plate, again showing the port and part of the rim. FIG.
Figure 3C:
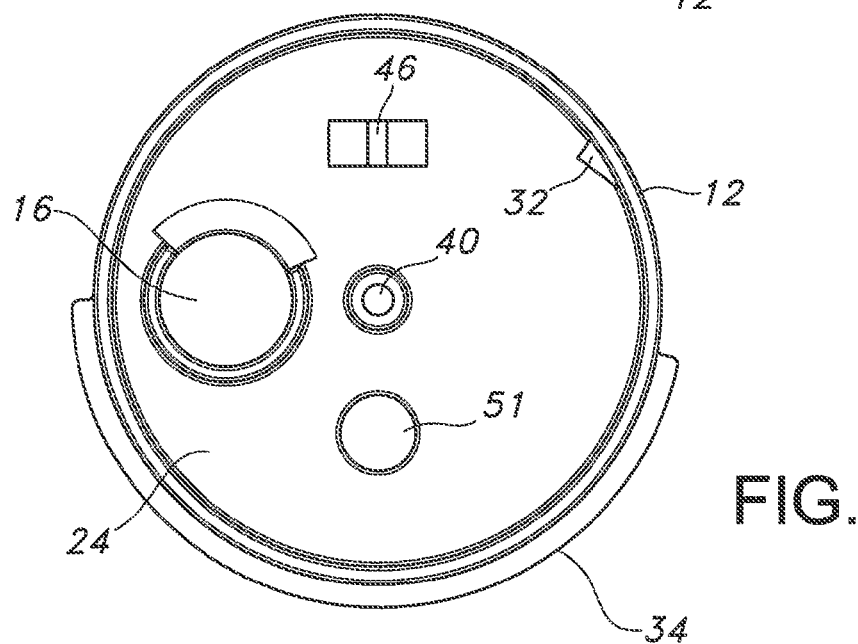
FIG. 3 includes three views of the distal plate.

The distal disk or plate 12 also has an exterior surface 22 which includes an outer perimeter 26 and a perimeter wall 28 which is desirably formed along the outer perimeter 26. The perimeter wall 28 may extend proximally away from the outer perimeter 26 at about a 90 degree angle (FIGS. 3B and 3C). The exterior surface 22 also has a rim 34 that extends the surface 22 outwardly for approximately 180 degrees of the plate 12 (FIGS. 3A, 4 and 2). The term "about", when placed adjacent a number/numeral, refers to the stated number plus or minus ten (10) percent of the stated number. The cuff 20 can extend through the interior surface 24 of the distal plate 12 in a proximal direction though it should have a cut-out portion 48 (FIG. 2) arranged so that the clutch 80 can contact a catheter (not shown) inserted through the port 16 (FIG. 4).

The perimeter wall 28 desirably is smooth. The interior surface 24 of the distal plate 12 includes a center alignment means or point 40, e.g. an aperture or recess in the plate (FIG. 3C) configured to receive a fastener 42, such as a screw or pin (not shown), a male coupling structure (not shown), a female coupling structure (not shown), or other coupling structure designed to match and secure a complementary coupling structure (not shown). The fastener 42 desirably holds the distal and proximal plates 12, 14 adjacent each other in a stacked configuration and axially aligned position, while permitting movement of each plate 12, 14 relative to the other.

As best seen in FIG. 4, the interior surface 24 of the distal plate 12 includes at least one raised portion, slope or ramp 46. This ramp cooperates with other components described below to assist in limiting the movement of the plates 12, 14 while an object is inserted through the port 16. The inner surface 30 of the perimeter wall 28 of the distal plate 12 also has a tooth 32 that also cooperates to limit the movement of the plates. The interior surface 24 of the distal plate 12 also has a pivot point 51 where the clutch 80 may be attached to the interior surface 24 of the distal plate 12. The clutch 80 may pivot back and forth about this point 51 during operation of the device. The clutch 80 does not, however, contact or interfere with the central alignment means 40 in any position of the distal and proximal plates 12, 14 but is designed to remain clear of the central alignment means 40 during operation. Such components and predetermined positions will be discussed in detail below.

The proximal disk or plate 14 includes a first port 50 and a second port 52, each having an opening extending through the proximal plate 14, as shown in FIGS. 5A-C. The first port 50 may have a first cuff 54 which is provided on an outer surface 56 of the proximal plate 14. The first cuff 54 may extend beyond an inner surface 58 as well. Similarly, the second port 52 may have a second cuff 62 which is provided on the outer surface 56 of the proximal plate 14. The second cuff 62 may, like the first cuff 54, extend beyond the inner surface 58. The inner surface 58 of the proximal plate 14 also has stops 72 that are raised from the surface 58 and serve to cooperate with the pin 92 of the clutch 80 to limit movement of the clutch 80.

The proximal plate 14 has an outer perimeter 64 which desirably includes a perimeter wall 66. The perimeter wall 66 may be formed along the outer perimeter 64 and it desirably extends distally away from the outer perimeter 64 at about a 90 degree angle. There is a tab 36 on the perimeter wall of the proximal plate 14 extending in a distal direction. The perimeter wall 28 of the distal plate 12 is sized to fit within the perimeter wall 66 of the proximal plate 14.

When the device is assembled, the tab 36 on the proximal plate 14 contacts the most distant ends of the rim 34 on the distal plate 12 such that the motion of the two plates 12, 14 relative to each other can be at most 180 degrees. The tab 36 and rim 34 are located so that the proximal port 50 and distal port 16 can align with each other at one extreme of movement of the plates 12, 14 and so that the proximal port 52 and distal port 16 can align with each other at the other extreme of movement of the plates 12, 14. In going from one proximal port 50, 52 aligned with the distal port 16 to the other proximal port 50, 52 aligned with the distal port 16 the motion of the plates relative to each other must be reversed since they may only move about 180 degrees in relation to each other. The two plates 12, 14 cannot rotate in a full circle relative to each other.

An opposite alignment means 69 is provided in the proximal plate 14, e.g. a center opening or protrusion (indicated in FIG. 5), a female coupling structure (not shown), a male coupling structure (not shown), or other coupling structure designed to match and secure a complementary coupling structure (not shown). The opposite alignment means 69 desirably aligns with the center alignment means 40 in the distal plate 12, and both are held at least adjacent each other by the fastener 42.

A clutch 80 is provided as shown in FIG. 7A-C. The clutch 80 has a proximal surface 82 and a distal surface 84. The distal surface 84 (FIG. 7C) has a pivot opening 86, e.g. an aperture through the clutch 80, which cooperates with the pivot point 51 of the interior surface 24 of the distal plate 12 to allow the clutch 80 to pivot. The clutch 80 has a tooth surface 88 that contacts the tooth 32 of the distal plate 12 to limit the movement of the clutch 80. The clutch 80 has a central opening area 90 that is designed to be large enough to avoid interference or touching of the clutch 80 to the assembled center alignment means 40 and the opposite alignment means 69 as the clutch 80 moves between the interior surface of the distal plate 12 and the inner surface of the proximal plate 14, as best seen in FIG. 4, when the plates are positioned as shown in FIG. 1. The clutch 80 has a pin 92 that limits the movement of the clutch 80 by contacting one of the stops 72 of the inner surface 58 of the proximal plate 14 when the plates are rotated relative to each other when a catheter 134 or similar elongated structure is inserted through the ports 16 and 50 or 16 and 52, as will be explained in more detail below. The pin 92 and stops 72 are sized such that they do not touch each other during normal operation, i.e. the pin 92 will pass below the stops 72 when the plates 12, 14 are rotated relative to each other if a catheter 134 or similar elongated structure is not inserted through the ports 16 and 50 or 16 and 52.

The clutch 80 also has a cut-out 94 that cooperates with the ramp 46 of the distal plate 12 to alter movement of the clutch 80 in the proximal and distal directions. The cut-out 94 need not be open entirely though the clutch 80 but can be a partial removal of clutch 80 material on the distal side of the plate 12. Likewise, the ramp 46 can be shaped differently. What is important is that the cut-out 94 and ramp 46 cooperate to move the clutch 80 toward the proximal plate 14 when the plates are rotated relative to each other.

The clutch 80 has a raised ring 96 on the proximal surface 82. The ring 96 serves to space the proximal surface 82 of the clutch 80 from the proximal plate 14 and also helps to limit the movement of the clutch 80 in cooperation with the other parts of the device. FIG. 6 shows the clutch 80 in relation to the proximal plate 14 as it would be after assembly (as shown in FIG. 1). The relationship of the ring 96 to the plate 14 may be seen in FIG. 6 as may be seen the relationship of the pin 92 with the stops 72.

In operation, a suction catheter assemblage 130 as partially illustrated in FIG. 1 may be releasably coupled to a port 50 at cuff 54 of assembly 10, which in turn is coupled to an endotracheal tube or artificial airway and a ventilator (not shown) at a distal end connector 132. At least a portion of the artificial airway is positioned in a portion of a patient's respiratory tract (not shown).

The suction catheter assemblage 130 also desirably includes an elongated catheter 134 having a lumen through it and an open proximal end (not shown). The proximal end of the suction catheter 134 or the suction catheter assemblage 130 is adapted to couple to at least a portion of a suctioning apparatus (not shown) which provides a suctioning force to the suction catheter 134. It will be appreciated that the suction catheter 134 has a length which is sufficient to extend through the assembly 10 and through any attached manifold and artificial airway so that it extends into a portion of a patient's respiratory tract in order to suction secretions. When the suction force is discontinued, the suction catheter 134 may then be withdrawn from the patient's respiratory tract, the artificial airway, the manifold, and the assembly 10. The suction catheter 134 is desirably returned to its position in its assembly 130. In this manner, the substantial length of the suction catheter 134 is positioned outside of the closed circuit ventilation system of the patient until needed again for suctioning secretions.

The suction catheter assemblage 130 may be coupled to either the first or the second cuff 54, 62 of the first or second ports 50, 52, respectively. Similarly, a bronchoscope, or other instrumentation, and so forth, may be releasably coupled to one of the first or second cuffs 54, 62 of the first or second ports 50, 52, respectively, as well. It will be appreciated that the suction catheter 134 and suction catheter assemblage 130 are maintained as a part of the closed circuit ventilation system at all times.

In a method of operation and use, a health care provider grasps the assembly 10 and rotates the proximal plate 14 such that the cuff 20 and port 16 of the distal plate 12 align with the first cuff 54 and first port 50 of the proximal plate 14. In this position a catheter 134 may be inserted through the ports 50, 16 and into the respiratory tract of the patient. When it is desired, the operation may be reversed and the catheter 134 withdrawn. The plates 12, 14 may again freely rotate about 180 degrees.

If, prior to withdrawal of the catheter 134, an attempt is made to rotate the plates in relation to one another, the tab 36 and the rim 34 will stop the movement in one direction and the clutch 80 will stop the operation in the other direction. The clutch 80 stops the movement of the plates 12, 14 prior to withdrawal of the catheter 134 because, in attempting to turn the plates 12, 14, the catheter 134 contacts the clutch 80 and moves it in a direction that causes the tooth surface 88 on the clutch 80 to contact the tooth 32 on the distal plate 12. The clutch 80 and distal plate 12 are thus unable to move relative to each other. At the same time as the clutch 80 is moved toward the tooth 32 by the inserted catheter 134, the clutch 80 also contacts the ramp 46 and this causes the clutch 80 to move up the ramp 46 toward the proximal plate 14. As the clutch 80 moves toward the proximal plate 14, the pin 92 on the clutch 80 moves upwardly until it is high enough to interfere with, i.e. touch, one of the stops 72 on the proximal plate 14; ring 96 is designed to allow this movement. When the pin 92 contacts a stop 72, the movement of the plates 12, 14 relative to each other ceases. Therefore a passive lock is provided by the cooperation of these components, which substantially prevents movement of the distal and proximal plates 12, 14 when an object is inserted through the ports 50, 16.

The withdrawal of the catheter 134 from the port permits the clutch 80 to move away from the tooth 32 on the inner surface of the perimeter wall of the distal plate 12, permits the clutch 80 to move down the ramp 46 and so drops the pin 92 below the level of the stops 72 and allows the plates to rotate relative to each other again.

This passive lock occurs similarly when an object is inserted through ports 52, 16. A health care provider is thereby prevented from inadvertently moving the distal and proximal plates 12, 14 when an object, such as a bronchoscope, a suction catheter, and so forth, is positioned through the aligned port 16 and a second port 52. Such a move, absent such a passive safety lock, would be likely to affect an object, for example, by cutting off a distal portion of such an object, which could be catastrophic for the patient. This passive lock is removed when the object is completely withdrawn from the aligned ports 16, 52 of the distal and proximal plates 12, 14 of the assembly 10. Withdrawal of the inserted object away from the inner surface 56 of proximal plate 14 permits movement of the clutch 80 in the same manner as described for withdrawal of the suction catheter 134.

The first position with alignment of port 16 and cuff 20 with the first port 50 and first cuff 54 are desirably positioned, for example, about 180 degrees apart from the second position, with alignment of port 16 and cuff 20 with second port 52 and second cuff 62. When the assembly 10 is positioned in the first position, the second port 52 and second cuff 62 are desirably blocked by a portion of the distal plate 12. Similarly, when the assembly 10 is position in the second position, the first port 50 and first cuff 54 are also desirably blocked by a portion of the distal plate. Such blocking helps to maintain PEEP pressure and to prevent confusion over which port is open by preventing introduction of an object, such as a suction catheter, bronchoscope, and so forth, into the blocked port.

The term and/or phrase "closed" or "closed position" and variations thereof, desirably refers to a position of one or more ports in which the port(s) are not aligned, so that no large object, such as a suction catheter, a portion of a bronchoscope, and so forth, may move through the referenced "closed" port(s). A port may be "closed" or "blocked" such that an object, such as those referenced previously, are blocked or prevented from moving through the port(s). The port may not be totally blocked or closed, however, and gases and/or liquid may, in at least some instances, continued to move through a blocked or closed port.

Certain components herein have been described and shown at certain angles. However, it will be understood that any component may be positioned at any angle or any combination of angles, so long as the assembly operates as shown and/or described herein.

It will also be understood that curved or arched plates, convex or concave disks or plates, or flat or planar disks or plates may be used herein. Further, the disks or plates may comprise any configuration, so long as they operate as shown and/or described herein. Similarly, the disks or plates may move in varying ways, that is, the disks or plates may rotate, pivot, slide, and move in any manner, and so forth, relative to each other, so long as they operate to achieve the result(s) as shown and/or described herein. If the distal and proximal plates are flat, square or rectangular plates (not shown), it will be appreciated that the distal and proximal plates may be positioned to slide relative to each other. One skilled in the art will understand the modifications which will be required to implement this and other alternative embodiments.

The assembly 10 may include more than one port and cuff on the distal disk or plate, and more than two ports and cuffs on the proximal disk or plate (not shown).

The phrase "operable communication" desirably refers to a transmission or passage between two points and/or two structures for a specific purpose. In this example, operable communication would be a passage which permits gasses and/or liquid(s) to pass, and may also be configured to permit objects to pass.

The terms "comprise," "comprises," "comprising" and other derivatives from the root term "comprise" desirably, are intended to be open-ended terms that specify the presence of any stated features, elements, integers, steps, or components, but do not preclude the presence or addition of one or more other features, elements, integers, steps, components, or groups thereof. Similarly, the terms "include", "includes", "including," as well as the terms "has", "have", "having", "is" and derivatives thereof, are intended to be interpreted as the word "comprise", and are intended to be open-ended terms that specify the presence of any stated features, elements, integers, steps, or components, but do not preclude the presence or addition of one or more other features, elements, integers, steps, components, or groups thereof.

While the present disclosure has been described in connection with certain preferred embodiments it is to be understood that the subject matter encompassed by way of the present disclosure is not to be limited to those specific embodiments. On the contrary, it is intended for the subject matter of the disclosure to include all alternatives, modifications and equivalents as can be included within the spirit and scope of the following claims.

What is claimed is:

1. A respiratory access assembly, comprising:
    a distal plate having a port, the port adapted to be positioned in operable communication with an artificial airway of a patient;
    a proximal plate including a first port and a second port, the distal plate positioned against the proximal plate in a stacked configuration, each plate configured to move; and
    a clutch positioned between the plates, the clutch cooperating with both plates to substantially prevent movement of the plates when the port of the distal plate is positioned in an alignment with at least one port of the proximal plate and an object is positioned through the aligned ports of the plates,
    wherein the clutch pivots about a point on the distal plate and contacts a tooth on the distal plate while simultaneously moving toward said proximal plate on a ramp on said distal plate, to prevent relative movement of the plates until the object is withdrawn.

2. The respiratory access assembly of claim 1, wherein the clutch is activated only when an object is positioned through the aligned ports to substantially prevent movement of the plates, thereby providing a passive lock.

3. The respiratory access assembly of claim 1, wherein the clutch contacts a stop provided on the proximal plate, the stop configured to prohibit movement of said clutch by acting on a pin on said clutch when an object is positioned through the aligned ports.

4. The respiratory access assembly of claim 1, wherein when the port of the distal plate and the first port of the proximal plate are aligned, the assembly is positioned in a first open position, and the clutch is activated to substantially prevent movement of the plates when an object is positioned through the aligned ports.

5. The respiratory access assembly of claim 1, wherein when the port of the distal plate is positioned between the first port and the second port of the proximal plate, no ports are aligned and each port is blocked.

6. A respiratory access assembly, comprising:
    two plates, each having a port, the plates positioned against each other in a stacked configuration, each plate configured to move relative to the other, the ports adapted to be aligned to be in operable communication with an artificial airway of a patient, and;
    a clutch positioned between said plates, the clutch attached to and pivotable about a point on one of the plates in response to an object positioned through the aligned ports; and,
    a passive lock for locking the plates together, including said clutch, to substantially prevent movement thereof when said object is positioned through the aligned ports, the passive lock unlocking the plates when said object is not positioned through the ports, wherein the plate with the point has a tooth and a ramp, and the clutch contacts the tooth while simultaneously moving on the ramp toward the other plate.

7. The respiratory access assembly of claim 6, wherein the clutch cooperates with both plates to substantially prevent movement of the plates when the port of one of the plates is positioned in an alignment with one of the ports of the other plate and an object is positioned through the aligned ports of the plates.

8. The respiratory access assembly of claim 6, wherein the other plate includes a stop, the stop configured to prohibit movement of said clutch by acting on a pin on said clutch when an object is positioned through the aligned ports.

* * * * *